(12) United States Patent
Ghanam et al.

(10) Patent No.: US 12,023,110 B2
(45) Date of Patent: Jul. 2, 2024

(54) SURGICAL TRACKER WITH EMITTERS TRIGGERED BY ELECTROMAGNETIC RADIATION

(71) Applicant: Stryker European Operations Limited, Carrigtwohill (IE)

(72) Inventors: Fadi Ghanam, Schallstadt (DE); Emeric Umbdenstock, Freiburg (DE)

(73) Assignee: Stryker European Operations Limited, Carrigtwohill (IE)

( * ) Notice: Subject to any disclaimer, the term of this patent is extended or adjusted under 35 U.S.C. 154(b) by 0 days.

(21) Appl. No.: 17/734,532

(22) Filed: May 2, 2022

(65) Prior Publication Data
US 2022/0354587 A1 Nov. 10, 2022

(30) Foreign Application Priority Data
May 4, 2021 (EP) .................................. 21172053

(51) Int. Cl.
*A61B 5/00* (2006.01)
*A61B 34/20* (2016.01)

(52) U.S. Cl.
CPC ............ *A61B 34/20* (2016.02); *A61B 5/6886* (2013.01); *A61B 2034/2051* (2016.02); *A61B 2034/2055* (2016.02); *A61B 2576/00* (2013.01)

(58) Field of Classification Search
CPC ............ A61B 34/20; A61B 2034/2051; A61B 2034/2055
See application file for complete search history.

(56) References Cited

U.S. PATENT DOCUMENTS

| | | | |
|---|---|---|---|
| 10,105,186 B2 | 10/2018 | Cheng et al. | |
| 2013/0342704 A1 | 12/2013 | Williams et al. | |
| 2015/0300816 A1* | 10/2015 | Yang | A61B 34/20 356/601 |
| 2019/0142525 A1* | 5/2019 | Malackowski | G01S 17/86 398/115 |
| 2019/0321108 A1* | 10/2019 | Ghanam | A61B 34/20 |

FOREIGN PATENT DOCUMENTS

| | | |
|---|---|---|
| WO | 9938449 A1 | 8/1999 |
| WO | 2011113482 A1 | 9/2011 |

* cited by examiner

*Primary Examiner* — Joel F Brutus
(74) *Attorney, Agent, or Firm* — Howard & Howard Attorneys PLLC (57) ABSTRACT

A tracker, a surgical tracking system, and a method for operating the tracker are provided. The tracker comprises an interface configured to attach the tracker to a surgical object that is to be tracked. The tracker further comprises circuitry comprising a detector configured to detect electromagnetic radiation, wherein the circuitry is configured to generate a trigger signal upon detection of a change of intensity of electromagnetic radiation by the detector. The circuitry further comprises a plurality of emitters configured to emit electromagnetic radiation, wherein the circuitry is configured to control the plurality of emitters to emit electromagnetic radiation responsive to the trigger signal.

20 Claims, 8 Drawing Sheets

SURGICAL TRACKER WITH EMITTERS TRIGGERED BY ELECTROMAGNETIC RADIATION

PRIORITY CLAIM

This application claims priority under 35 U.S.C. § 119 to European Patent Application No. 21172053.7, filed May 4, 2021, the entire contents of which are hereby incorporated by reference.

TECHNICAL FIELD

The present disclosure generally relates to a tracker for a surgical tracking system. In particular, a tracker with emitters triggered by electromagnetic radiation, a surgical tracking system comprising the tracker, and a method of operating the tracker are presented.

BACKGROUND

Surgical tracking systems are typically configured to track surgical objects such as a surgical instrument or a patient in an operating room. A common tracking technique involves an active tracker with emitters of electromagnetic radiation as well as a camera capable of detecting the electromagnetic radiation emitted by the tracker. Based on the detected electromagnetic radiation, the tracking system determines information on one or both of a position and an orientation of the tracker and, thus, of the surgical object to be tracked.

Active trackers need to operate reliably for the duration of an entire surgery, which can last up to a few hours. In order to provide sufficient power to operate the emitters of the tracker, the tracker may comprise a power line coupled to a socket. However, a power line will negatively affect handling of the tracker.

Another approach is to power the tracker with a battery and to control the emitters to emit pulsed electromagnetic radiation so as to reduce power consumption. In such a case, the emitters need to pulse in synchronicity with camera operation (e.g., in terms of an exposure timing). In such an implementation, the tracker requires a dedicated communication and processing device in order to receive and process operational parameters of the camera. Such a device increases power consumption, weight and material cost of the tracker. Especially for a disposable tracker, these factors are to be minimized.

U.S. Pat. No. 10,105,186 B2 discloses an inverse virtual rigid body optical tracking system which includes a laser-based scanning light source for scanning an area in which an operator utilizes a tool to be tracked. Three or more photodiodes are mounted on a tool surface. When the system operates, the scanning light source scans the work area. Once an individual photodiode detects the laser illumination, the orientation of the scanning beam is recorded by the system. Given a pre-calibrated spatial registration between the photodiodes and the tool, the tool position and orientation can be derived from the three beam orientation records, which indicate the laser beam scans over the three photodiodes. The tracking system determines the position of each photodiode based on time resolved signalling, which is requires significant processing resources. Moreover, the laser-based scanning light source is a complex and, thus, costly device.

SUMMARY

There is a need for a tracking technique that solves one or more of the aforementioned or other problems.

According to a first aspect, a tracker for a surgical tracking system is provided. The tracker comprises an interface configured to attach the tracker to a surgical object that is to be tracked. The tracker further comprises circuitry. The circuitry comprises a detector configured to detect electromagnetic radiation, wherein the circuitry is configured to generate a trigger signal upon detection of a change of an intensity of electromagnetic radiation by the detector. The circuitry further comprises a plurality of emitters configured to emit electromagnetic radiation, wherein the circuitry is configured to control the plurality of emitters to emit electromagnetic radiation responsive to the trigger signal.

The detection of a change of an intensity of electromagnetic radiation may be a binary detection (e.g., based on an on/off state of a source of electromagnetic radiation). The detection of a change of an intensity of electromagnetic radiation may be based on a threshold criterion. The threshold criterion may comprise an intensity threshold. Alternatively, the threshold criterion may comprise a threshold for a rate of change of radiant intensity.

The circuitry may be configured to generate the trigger signal only upon detection of an increase of the intensity of electromagnetic radiation by the detector (e.g., when a source of electromagnetic radiation switches from an off-state to an on-state). The detection of an increase of the intensity may be based on at least one of detection that the intensity exceeds a threshold intensity.

Alternatively, the circuitry may be configured to generate the trigger signal only upon detection of a decrease of the intensity of electromagnetic radiation by the detector (e.g., when a source of electromagnetic radiation switches from an on-state to an off-state). The detection of a decrease of the intensity may be based on at least one of detection that the intensity falls below a threshold intensity.

The circuitry may be configured to generate the trigger signal for a duration that the detector is subsequently (i.e., after an initial intensity change, such as from an off-state to an on-state) not detecting a (further) change of the intensity of electromagnetic radiation (e.g., from the on-state back to the off-state). The detector may, for example, detect no change of the intensity of electromagnetic radiation when the intensity of the electromagnetic radiation continues to exceed or stay below the intensity threshold.

The circuitry may be configured to generate the trigger signal for a predetermined time duration. The predetermined time duration may be below 10 ms and, for example, above 5 μs. The predetermined time duration may be between 100 μs and 1 ms (e.g., may be set to approximately 200 to 400 μs).

In response to the trigger signal, all the emitters may be controlled to emit electromagnetic radiation. The detector may comprise a single radiation-sensitive element associated with at least a subset of emitters, wherein the subset comprises more than one emitter of the plurality of emitters. The subset may comprise all emitters of the plurality of emitters. The circuitry may comprise more than one subset of emitters, wherein each subset comprises more than one emitter of the plurality of emitters. The circuitry may comprise for each subset of emitters a radiation-sensitive element associated with the subset of emitters. A first subset of emitters and a first radiation-sensitive element assigned thereto may be arranged on a first face of the tracker. A second subset of emitters and a second radiation-sensitive element assigned thereto may be arranged on a second face of the tracker, wherein the first and second face are arranged at an angle (e.g., in a range from 90° to 120°) to each other.

The circuitry may comprise a photodiode or phototransistor that comprises the radiation-sensitive element. The radiation-sensitive element may comprise a semiconductor material.

The tracker may comprise at least one battery for powering the circuitry. The battery may be at least one of an AAA battery or a button cell battery. The battery may be a CR2032 type button cell battery.

The tracker may comprise a wireless power reception device configured to receive power wirelessly. The wireless power reception device may comprise at least one of a coil for inductive coupling and an electrode for capacitive coupling.

The circuitry may comprise a switch (e.g., including one or more transistors) configured to control a current passing through the emitters responsive to the trigger signal. The switch may comprise a phototransistor.

The detector may be configured to detect infrared light. Alternatively or additionally, the plurality of emitters may be configured to emit infrared light.

Each of the plurality of emitters may comprise a light emitting diode, LED. The circuitry may be configured to limit a current through each of the LEDs to a current below 10 mA (and, e.g., above 1 mA). The circuitry may be configured to limit the current through each of the LEDs to a current of 3 mA or less. The circuitry may be configured to apply a voltage of 1.25V or less to each LED.

According to a second aspect, a surgical tracking system is provided. The surgical tracking system comprises a tracker as described herein and a camera with at least one image sensor configured to detect electromagnetic radiation emitted by the tracker of the surgical tracking system, and to generate image data based on the detected electromagnetic radiation. The camera has an exposure timing defining exposure time durations in which the at least one image sensor of the camera is sensitive to electromagnetic radiation. The surgical tracking system further comprises a source of electromagnetic radiation and a controller configured to control the source of electromagnetic radiation to emit pulses of electromagnetic radiation in synchronicity with the exposure timing. The surgical tracking system also comprises a processor configured to determine positional data of the tracker based on the image data.

The exposure timing may define a cyclic exposure of the at least one image sensor at a first frequency. A second frequency may define a rate of repetition of a periodic change of the intensity of the electromagnetic radiation emitted by the source of electromagnetic radiation. The first frequency may be identical to the second frequency. Alternatively, the first frequency may be a multiple of the second frequency. Further alternatively, the second frequency may be a multiple of the first frequency.

The controller may be configured to control a pulse duration of the pulsed electromagnetic radiation to lie between a tenth and ten times the exposure time of the camera. The duration of the pulsed electromagnetic radiation may be at least essentially identical to the exposure time of the camera. The controller may be configured to control the pulse duration dependent an intensity of electromagnetic radiation emitted by the emitters. The controller may be configured to control the pulse duration according to a function so that it decreases with (e.g., inversely proportional to) an increasing intensity of electromagnetic radiation emitted by the emitters.

The controller may be configured to control the source of electromagnetic radiation to emit pulses of electromagnetic radiation at least during some of the exposure time durations. In such a case, there may be an at least partial overlap between the pulses and the exposure time durations. Alternatively, the controller may be configured to control the source of electromagnetic radiation to emit pulses of electromagnetic radiation at least between some of the exposure time durations. In such a case, there may be no overlap between the pulses and the exposure time durations.

The exposure time duration may range between 50 μs and 1 ms. The exposure time duration may be set to approximately 200 μs to 400 μs. The camera may have a non-exposure timing defining non-exposure time durations in which the at least one image sensor of the camera is not sensitive to electromagnetic radiation. The non-exposure timing may range between 500 μs and 1.9 ms. The non-exposure timing may be 1.7 ms. A frame rate of the camera range between 100 Hz and 2 kHz, for example between 300 Hz and 600 Hz.

The source of electromagnetic radiation may be configured to flood an entire surgical site in which the tracker is operated with electromagnetic radiation. The source of electromagnetic radiation may cover a solid angle between 2 n and 0.05 sr.

The surgical tracking system may further comprise an output device configured to output navigation instructions based on the positional data of the tracker as determined by the processor. The output device may comprise at least one of a display, a speaker, virtual reality glasses, glasses with a head-up-display, and a haptic feedback device.

According to a third aspect, a method for operating a tracker attached to a surgical object is presented. The tracker comprises circuitry comprising a detector and a plurality of emitters configured to emit electromagnetic radiation. The method comprises generating a trigger signal upon detection of a change of an intensity of electromagnetic radiation by the detector. The method further comprises controlling, by the circuitry, the plurality of emitters to emit electromagnetic radiation responsive to the trigger signal.

The method may comprise detecting electromagnetic radiation emitted by the tracker of the surgical tracking system, and generating image data based on the detected electromagnetic radiation. Those steps may be performed using a camera having an exposure timing defining exposure time durations in which at least one image sensor of the camera is sensitive to electromagnetic radiation.

BRIEF DESCRIPTION OF THE DRAWINGS

Further details, advantages and aspects of the present disclosure will become apparent from the following embodiments taken in conjunction with the drawings, wherein.

DETAILED DESCRIPTION

Figure 1:
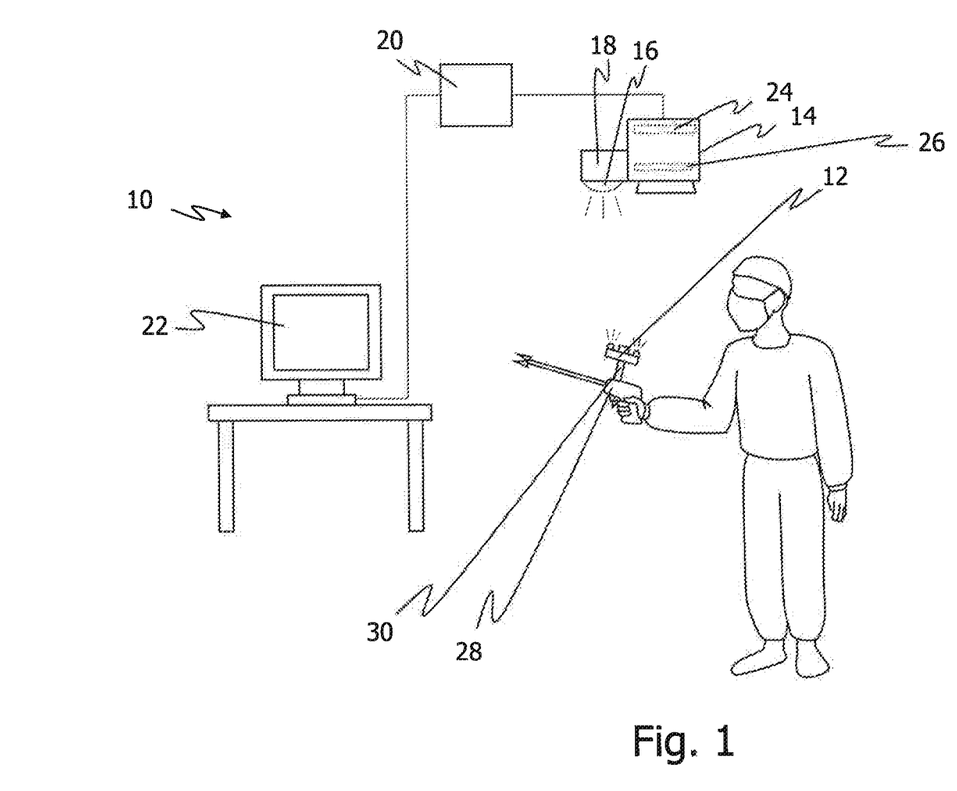
FIG. 1 schematically shows a surgical tracking system according to an embodiment of the present disclosure.

FIG. 1 schematically shows an embodiment of a surgical tracking system 10 that is installed at a surgical site (e.g., in an operating room). The surgical tracking system 10 comprises a tracker 12, a camera 14, a source of electromagnetic radiation 16, a controller 18, and a processor 20. The tracking system 10 is coupled to an output device 22 that is configured to output navigation instructions to a surgeon. As such, the tracking system 10 and output device 22 form a surgical navigation system.

In FIG. 1, the processor 20 is provided by a local computer system. Alternatively, the processor 20 may be provided by a remote server or cloud computing resources. In FIG. 1, the processor 20 and the controller 18 are two separate devices. Alternatively, the processor 20 and the controller 18 may be provided by or be part of a single device.

The processor 20 is communicatively coupled with the output device 22. The output device depicted in FIG. 1 comprises a display. Alternatively or additionally, the output device may comprise at least one of a speaker, virtual reality glasses, glasses with a head-up-display, and a haptic feedback device.

The camera 14 depicted in FIG. 1 has at least one image sensor 24 such as a charged couple device (CCD) or a complementary metal-oxide-semiconductor sensor (CMOS). In some variants, the camera 14 may have multiple image sensors 24. In particular, the camera 14 may be a stereo camera with at least two image sensors 24.

The image sensor 24 is configured to generate image data based on detected electromagnetic radiation. The image sensor 24 can be repeatedly exposed to electromagnetic radiation in order to generate image data for multiple images. In order to control the exposure of the image sensor 24, the camera 14 depicted in FIG. 1 has a shutter 26. The shutter 26 is an electronic shutter. Alternatively, the camera 14 may have a mechanical shutter.

The camera 14 is operable at an exposure timing defining exposure time durations in which the at least one image sensor 24 is sensitive to electromagnetic radiation. Each exposure time duration may be defined by a time duration in which a mechanical shutter is open or the image sensor 24 is active (when using an electronic shutter). The camera 14 further is associated with a non-exposure timing defining non-exposure time durations in which the at least one image sensor 24 of the camera 14 is not sensitive to electromagnetic radiation. Each non-exposure time duration may be defined by a time duration in which a mechanical shutter is closed or the image sensor 24 is not active (when using an electronic shutter). The camera 14 is configured to cyclically assume exposure and non-exposure states.

An exposure time duration and a non-exposure time duration combine to a frame duration. A number of frames captured by the camera 14 in a given period of time is commonly referred to as frame rate. For example, the camera 14 may have a frame rate of 500 Hz with a frame duration of 2 ms. The frame duration may cover an exposure time duration of 300 μs and a non-exposure time duration of 1.7 ms.

The source of electromagnetic radiation 16 is configured to emit electromagnetic radiation. The source of electromagnetic radiation 16 may in particular be configured to emit at least one of infrared light, visible light, ultraviolet light, and X-rays. As will be explained further below, the electromagnetic radiation triggers the tracker 12. Therefore, the electromagnetic radiation emitted by the source of electromagnetic radiation 16 does not require to be visible to a surgeon. For example, the source of electromagnetic radiation 16 may emit infrared light in order to not distract the surgeon. Alternatively, the source of electromagnetic radiation 16 may emit visible light (e.g., in order to provide illumination of the surgical site).

The source of electromagnetic radiation 16 is specifically configured to flood the entire surgical site with electromagnetic radiation. The source of electromagnetic radiation 16 may therefore emit non-directed electromagnetic radiation.

In this regard the source of electromagnetic radiation 16 may cover a solid angle between 2 n and 0.05 sr (e.g., between π, or 0.5 π, and 0.1 sr). As an example, an emission angle in a plane intersecting the tracker 12 may be larger than 30°, and in particular larger than 60°.

The controller 18 is configured to control the source of electromagnetic radiation 16 to emit pulsed electromagnetic radiation. The pulses may be generated by pulsing power provided to the source of electromagnetic radiation 16. Alternatively or additionally, a shutter may be provided between the source of electromagnetic radiation 16 and the surgical site, wherein the shutter is configured to periodically open and close. The shutter may comprise a mechanical shutter or an optically active element such as a liquid crystal cell.

The controller 18 is configured to control the source of electromagnetic radiation 16 to emit pulses of electromagnetic radiation in synchronicity with the exposure timing of the at least one image sensor 24. Therefore, if the exposure timing defines a cyclic exposure of the at least one image sensor 24 at a first frequency, the controller 18 is configured to control the source of electromagnetic radiation 16 to emit pulses in a second frequency that is equal to (or a multiple of) the first frequency. The exposure timing (i.e., the first frequency) may be defined by the frame rate of the camera 14

In some variants, the controller 18 is configured to control the source of electromagnetic radiation 16 to emit pulses of electromagnetic radiation such that the exposure time durations temporally overlap at least partially with the pulses of electromagnetic radiation. Since the pulses of electromagnetic radiation are emitted in synchronicity with the exposure timing, every exposure duration temporally overlaps at least partially with a pulse of electromagnetic radiation (assuming that the second frequency equals the first frequency). In other variants, the controller 18 is configured to control the source of electromagnetic radiation 16 to emit pulses of electromagnetic radiation such that the exposure time durations temporally do not overlap with the pulses of electromagnetic radiation.

The tracker 12 depicted in FIG. 1 is attached to a surgical instrument 28. To this end, the tracker 12 has an interface 30. The interface 30 may comprise at least one of a clamp, a screw, a magnet, an opening, and an adhesive. The interface 30 may be configured for attaching the tracker 12 to any other surgical object such as a patient, a surgery table, or other reference frame. In particular, the tracker 12 may be configured to be attached to a patient (not shown). As an example, the tracker 12 may comprise an interface that includes an adhesive for sticking the tracker 12 to the patient's skin. In another variant, the tracker 12 comprises an interface for anchoring the tracker at or in a bone.

Figure 2A:
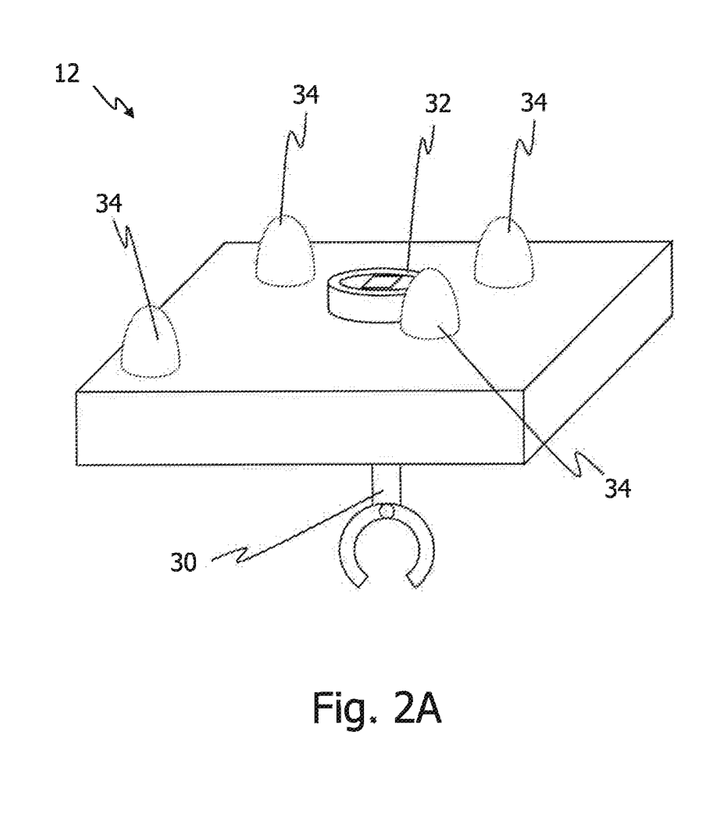
FIG. 2A shows a perspective view of a tracker according to an embodiment of the present disclosure.
Figure 2B:
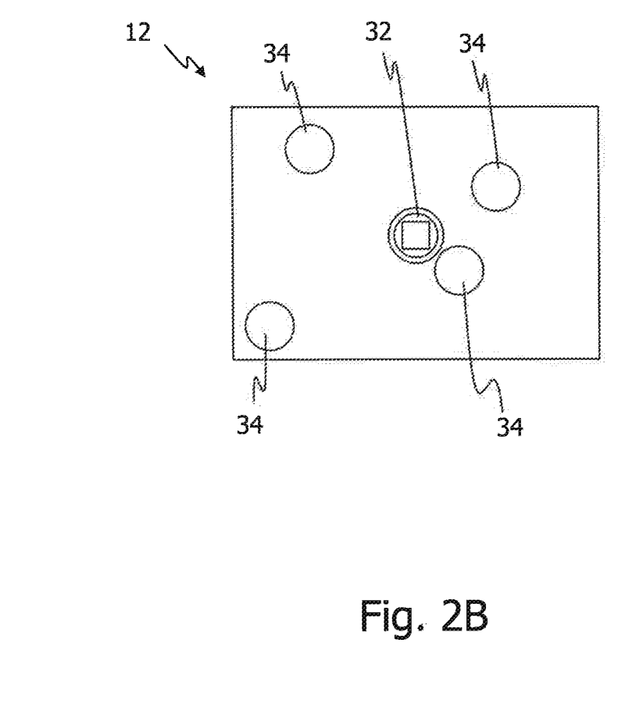
FIG. 2B shows a top view of the tracker of FIG. 2A.

FIG. 2A shows a perspective view of the tracker 12. FIG. 2B shows a top view of the tracker 12. As illustrated in FIGS. 2A and 2B, the tracker 12 comprises circuitry comprising a detector 32 configured to detect electromagnetic radiation. The detector 32 may comprise at least one of a photodiode, a phototransistor, a photoresistor, or any other device that is suitable to convert electromagnetic radiation into an electrical signal.

The tracker 12 further comprises a plurality of emitters 34 configured to simultaneously emit electromagnetic radiation. Based on a pre-defined geometrical arrangement of the emitters 34, positional data of the tracker 12 can be determined by the tracking system 10. The positional data of the tracker 12 may include at least one of a position and orientation of the tracker 12. Based on a known relationship of the tracker 12 to the object to be tracked (e.g., the surgical instrument 28), the tracking system 10 may further determine at least one of a position and orientation of the object.

The tracker 12 depicted in FIGS. 2A and B comprises four emitters 34. Providing at least three emitters 34 allows determining positional data including both the position and orientation. The fourth emitter 34 offers redundancy for improved accuracy and reduces errors when line of sight of an emitter 34 is lost. In some variants, the tracker 12 may have only two emitters 34 for tracking with a lower degree of freedom or more than four emitters (such as five, six or seven emitters 34) for an improved accuracy. The emitters 34 depicted in FIGS. 2A and B are arranged in a pattern with no rotational symmetry, such that there is no rotation of the pattern with an angle smaller than 360° that results in an identical overlay with the pattern before rotation.

Each emitter 34, or at least one or more of the emitters 34, comprises a light emitting diode (LED). Each, or at least one or more, of the emitters 34 may comprise an organic LED, a polymer LED, and an active-matrix LED.

The emitters 34 are configured to emit at least one of infrared light, visible light, ultraviolet light, and X-rays. The emitters 34 may have at least essentially identical emission spectra or different emission spectra. For example, all emitters 34 may be configured to emit infrared light. Alternatively, at least one of the emitters 34 may be configured to emit visible light, whereas the remaining emitters 34 emit infrared light.

FIGS. 3A-F show different embodiments of a circuitry 36 of the tracker 12. Use of a tracker 12 with such circuitry 36 in combination with other components of the surgical tracking system 10 and the resulting advantages will be described later with reference to FIGS. 5 and 6A-F.

Figure 3A:
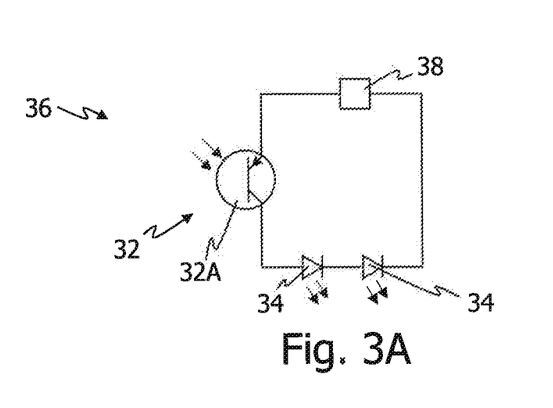
FIG. 3A shows a circuit diagram of a first embodiment of a tracker circuitry.

FIG. 3A shows a circuit diagram of a first embodiment for circuitry 36 of the tracker 12. The circuitry 36 has two emitters 34 in form of infrared LEDs. As explained above, any other type of emitter 34 and/or more than two emitters 34 may be provided instead. The emitters 34 shown in FIG. 3A are electrically connected in series, resulting in a circuitry with low complexity. Alternatively, at least one of the emitters 34 may be electrically connected in parallel to the remaining emitters 34, ensuring operation of the at least one emitter 34 in case one of the other emitters 34 fails.

The circuitry 36 further comprises a power source 38. The power source 38 may comprise a battery such as an AAA battery or button cell battery (e.g., a CR2032 type battery). Alternatively or additionally, the power source 38 may comprise a wireless power reception device configured to receive power wirelessly. The wireless power reception device may be configured to receive power using inductive coupling or capacitive coupling.

The circuitry 36 depicted in FIG. 3A also comprises the detector 32 (see FIGS. 2A and 2B) in form of a phototransistor 32A. It should be noted that FIGS. 3A-F and 4A and B depict the symbol of an NPN transistor. However, the circuitry 36 can also be realized with a PNP transistor. Also, the circuitry 36 may comprise any other type of switch (e.g., a switch realized by a plurality of transistors or any other semiconductor element(s)).

In general, a transistor has three terminals, wherein a current flow between a first and second terminal can be controlled by a control voltage applied at the third terminal. In the context of a bipolar transistor, these terminals are commonly labelled collector, emitter, and base. In the case of a field-effect transistor, the three terminals are typically labelled source, drain, and gate. Within this description, the terminals are called collector, emitter, and base. However, it should be understood that these terms do not limit the present invention to bipolar transistors, but that any other type of transistor can be used and that reference is made to the corresponding terminals of such other type of transistor.

The phototransistor 32A of FIG. 3A is a type of transistor with a radiation-sensitive element, wherein photons impinging onto the radiation-sensitive element generate electrons and/or electron holes, which are injected into the base. As a result, a larger current can pass between the source and drain when electromagnetic radiation impinges onto the radiation-sensitive element. The phototransistor 32A may be sensitive to a specific spectrum of electromagnetic radiation, e.g., using a filter for specific wavelengths or using a material for the radiation-sensitive element that absorbs specific wavelengths. Therefore, the phototransistor 32A may be sensitive only to electromagnetic radiation of a specific spectrum (e.g., infrared light, visible light, infrared light, or X-rays). For example, the phototransistor 32A may only be sensitive to infrared light (e.g., 700 nm to 1000 nm) or to a specific infrared wavelength (e.g., 800 nm). Such a phototransistor 32A would not switch to a conducting state when exposed to visible light of ambient lighting. Therefore, such a phototransistor 32A is less prone to unintended switching when exposed to ambient lighting.

Since the phototransistor 32A is electrically connected between the power source 38 and the emitters 34, the phototransistor 32A is configured to switch on and off operation of the emitters 34, wherein the emitters 34 emit electromagnetic radiation in an on-state of the circuitry 36 and do not emit electromagnetic radiation in an off-state of the circuitry 36. The circuitry 36 is therefore configured to generate a trigger signal in form of a voltage applied at the base of the phototransistor 32A, wherein the applied voltage is the result of electromagnetic radiation impinging onto the radiation-sensitive element of the phototransistor 32A.

It should be noted that in the examples depicted in FIGS. 3A-F and 4A and B, the circuitry 36 has a detector 32 with a single photo-sensitive element that is associated with all emitters 34 and, in more detail, configured to control operation of all emitters 34 simultaneously. Alternatively, the detector 32 may comprise a plurality of photo-sensitive elements each associated with a subset of the emitters 34. Further alternatively, the detector 32 may comprise a single photo-sensitive element that is associated only with a subset of the plurality of emitters 34.

Figure 3B:
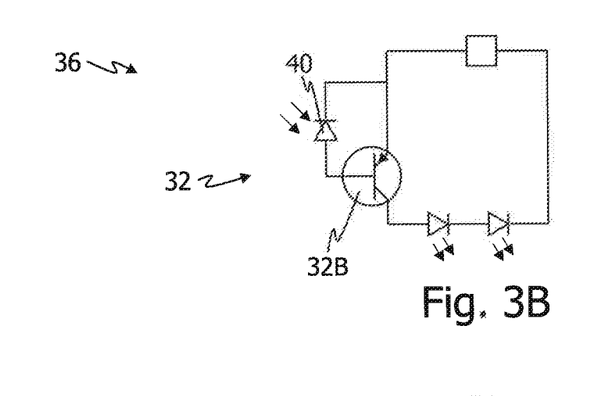
FIG. 3B shows a circuit diagram of a second embodiment of a tracker circuitry.

FIG. 3B shows a circuit diagram for a second embodiment of the circuitry 36 of the tracker 12. The first and second embodiments of the circuitry 36 essentially differ in the type of detector 32. The detector 32 of the first embodiment comprises (or consists of) a phototransistor 32A, whereas the detector 32 of the second embodiment comprises (or consists of) a transistor 32B and a photodiode 40 that is electrically connected to the base of the transistor 32B. When electromagnetic radiation impinges onto a radiation-sensitive element of the photodiode 40, the radiation-sensitive element generates electrons and/or electron holes, which are injected into a base of the transistor 32B. Therefore, the second embodiment of the circuitry 36 operates in a similar manner as the first embodiment. However, the radiation-sensitive element and the transistor are separated in two dedicated components.

The first circuitry embodiment only has one component and is, therefore, less complex. The second circuitry embodiment is more flexible, as different types of photodiodes and transistors can be combined. For example, a plurality of trackers 12 may be manufactured with identical transistors, but provided with different photodiodes that are sensitive to different spectra of electromagnetic radiation. Another advantage of a separation of photodiode 40 and transistor 32B is that additional circuit devices (not shown) for modifying the electrical signal of the photodiode 40 can be arranged between the photodiode 40 and the transistor 32B.

Figure 3C:
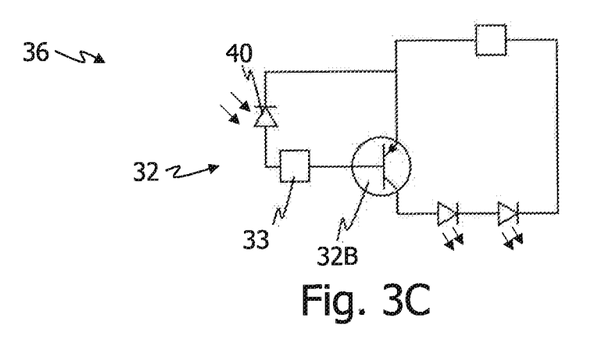
FIG. 3C shows a circuit diagram of a third embodiment of a tracker circuitry.

FIG. 3C shows a circuit diagram for a third embodiment of the circuitry 36 of the tracker 12. The third embodiment of the circuitry 36 essentially differs from the second embodiment in a signal generator 33 that is coupled between the photodiode 40 and the transistor 32B. The signal generator 33 is configured to generate the trigger signal for a predetermined time duration. Therefore, the circuitry 36 does not generate the trigger signal for the duration that the detector 32 is detecting electromagnetic radiation, but for the predetermined time duration. As such, the predetermined duration of operating the emitters 34 can be decoupled from (i.e., may be smaller than) the on-duration of the source of electromagnetic radiation 16. The predetermined time duration may lie in a range of 5 µs to 10 ms, e.g., 300 µs.

The signal generator 33 may comprise a monostable multivibrator. A monostable multivibrator is a circuit element with a stable first state that can be temporarily switched to a second state. To this end, the monostable multivibrator commonly comprises a two transistor cross-coupled switching circuit designed so that one or more of its outputs are fed back as an input to the other transistor with a resistor and capacitor network. The duration for the temporary second state can be adjusted by a capacity of the capacitator. The stable first state may be assigned to an off-state of the circuitry 36 and the temporary second state may be assigned to the on-state of the circuitry 36.

Figure 3D:
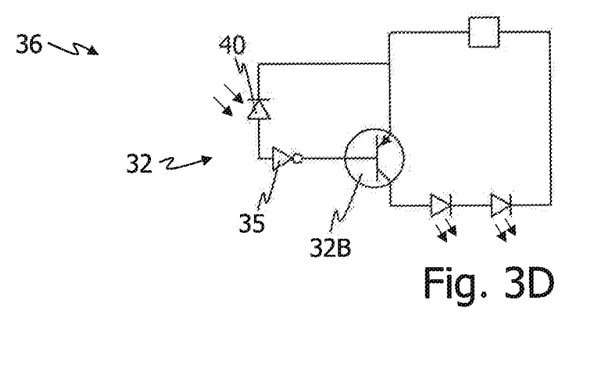
FIG. 3D shows a circuit diagram of a fourth embodiment of a tracker circuitry.

FIG. 3D shows a circuit diagram for a fourth embodiment of the circuitry 36 of the tracker 12. The fourth embodiment of the circuitry 36 essentially differs from the second embodiment in an inverting element 35 coupled between the photodiode 40 and the transistor 32B. When the photodiode 40 does not detect electromagnetic radiation, the inverting element 35 generates a trigger signal that switches the transistor 32B to the on-state, wherein a current passes through the emitters 34. When the photodiode 40 detects electromagnetic radiation, the inverting element 35 generates an electrical signal that switches the transistor 32B to the off-state.

The signal generator 33 and the inverting element 35 are not exclusive to each other and may be combined. Alternatively or additionally, other electrical components may be arranged between the photodiode 40 and the transistor 32B such as at least one of a signal amplifier, a noise filter, and a resistor.

Figure 3E:
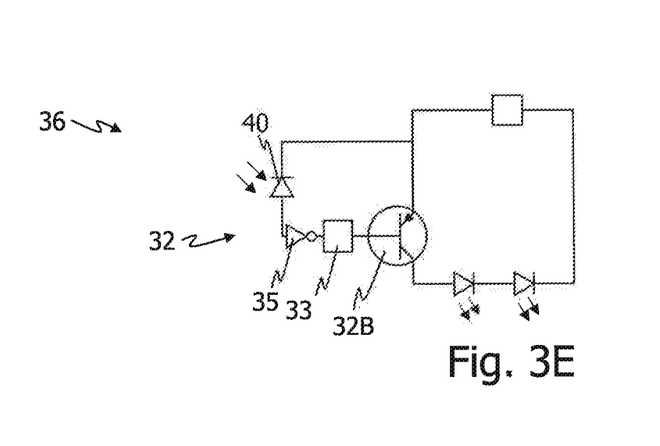
FIG. 3E shows a circuit diagram for a fifth embodiment of a tracker circuitry.

FIG. 3E shows a circuit diagram for a fifth embodiment of the circuitry 36 of the tracker 12. The fifth embodiment is, in essence, a combination of the third and fourth embodiments, as the circuitry 36 comprises both the signal generator 33 and the inverting element 35 coupled between the photodiode 40 and the transistor 32B. As a result, the circuitry 36 is configured to generate the trigger signal only upon detection of a decrease of the intensity of electromagnetic radiation by the detector (due to the inverting element 35) and to generate the trigger signal for a predetermined time duration (due to the signal generator 33).

Figure 3F:
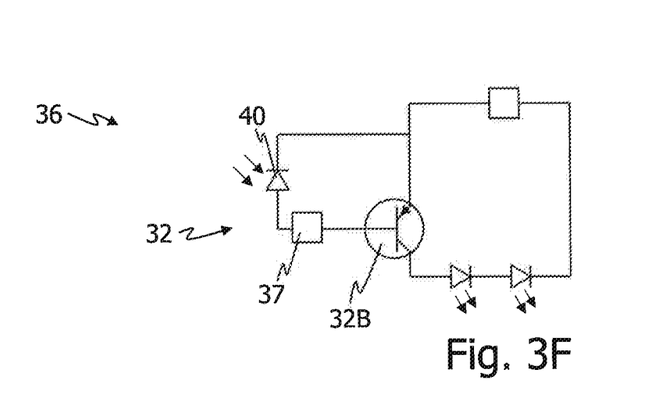
FIG. 3F shows a circuit diagram for a sixth embodiment of a tracker circuitry.

FIG. 3F shows a circuit diagram for a sixth embodiment of the circuitry 36 of the tracker 12. The sixth embodiment of the circuitry essentially differs from the second and fourth embodiment in that the circuitry 36 is configured to generate a trigger signal when the detector 32 detects an increase as well when the detector 32 detects a decrease of the intensity of electromagnetic radiation. To this end, the circuitry comprises a trigger generator 37 coupled between the photodiode 40 and the transistor 32B. The trigger generator 37 is configured to generate a trigger signal upon a change of a voltage generated by the photodiode 40. Furthermore, the trigger generator 37 is configured to generate a trigger signal for a predetermined duration (of, e.g., 100 to 500 µs). As a result, the trigger generator 37 is configured to generate a trigger signal for the predetermined duration when electromagnetic radiation starts impinging onto the radiation-sensitive element of the photodiode 40 and when electromagnetic radiation stops impinging onto the radiation-sensitive element of the photodiode 40.

Figure 4A:
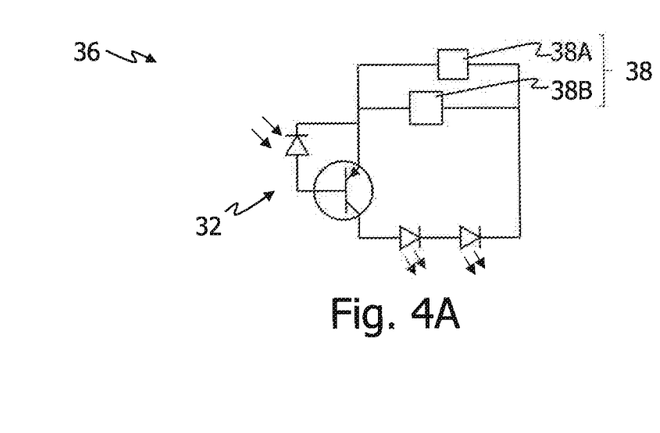
FIG. 4A shows a circuit diagram of a seventh embodiment of a tracker circuitry.

FIG. 4A shows a circuit diagram for a seventh embodiment for the circuitry 36 of the tracker 12. The seventh embodiment of the circuitry 36 essentially differs from the second embodiment in that the power source 38 has an energy supply 38A and an energy storage 38B. The energy supply 38A may be a power line to a power socket or to a surgical instrument (see reference numeral 28 in FIG. 1). The energy storage 38B is a device that holds a finite amount of electrical energy. The energy storage 38B may comprise at least one of a non-chargeable battery, a chargeable battery, and a capacitor. The circuitry 36 may be powered by the energy supply 38A while being connected to the power line. The energy storage 38B may be used to power the circuitry 36 when disconnected from the power line. The chargeable battery and/or capacitor of the energy storage 38B may be configured to be chargeable by the energy supply 38A.

Figure 4B:
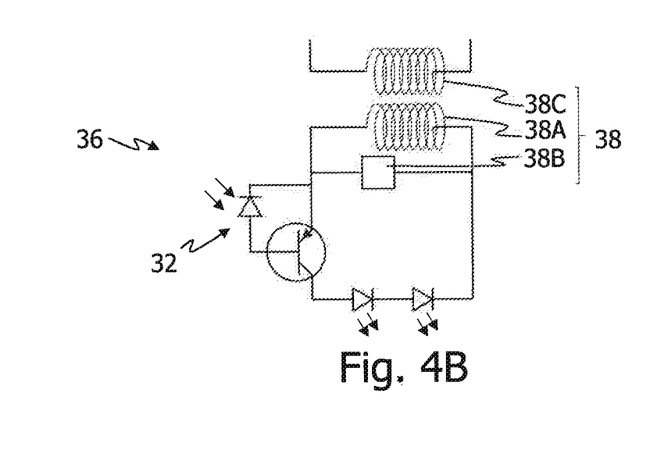
FIG. 4B shows a circuit diagram of a eights embodiment of a tracker circuitry.

FIG. 4B shows a circuit diagram for an eighth embodiment of the circuitry 36 of the tracker 12. The eighth embodiment differs from the seventh embodiment in that the energy supply 38A comprises a wireless power reception device 38B configured to receive power wirelessly from a wireless power transfer device 38C. The surgical instrument 28 (see FIG. 1) comprises the wireless power transfer device 38C. To this end, the tracker 12 is attached to the surgical instrument 28 by the interface 30 (see FIG. 2A). In order to shorten a distance between the wireless power reception device 38B and the wireless power transfer device 38C, the wireless power reception device 38B may be arranged inside or at a distal end of the interface 30.

The wireless power transfer depicted in FIG. 3D is realized by inductive coupling between coils of the wireless power reception device 38B and of the wireless power transfer device 38C. Alternatively or additionally, the wireless power transfer may be realized by capacitive coupling between electrodes of the wireless power reception device 38B and of the wireless power transfer device 38C.

As described above, the controller 18 is configured to control the source of electromagnetic radiation 16 to emit pulses of electromagnetic radiation in synchronicity with the exposure timing of the camera 14, and the tracker 12 is configured to emit electromagnetic radiation when triggered by an intensity change of the detected electromagnetic radiation. As a result, the controller 18 can cause the tracker 12 to emit electromagnetic radiation during exposure time durations of the camera 14, wherein the tracker 12 performs a method 100 as will now be described with reference to FIG. 5.

Figure 5:
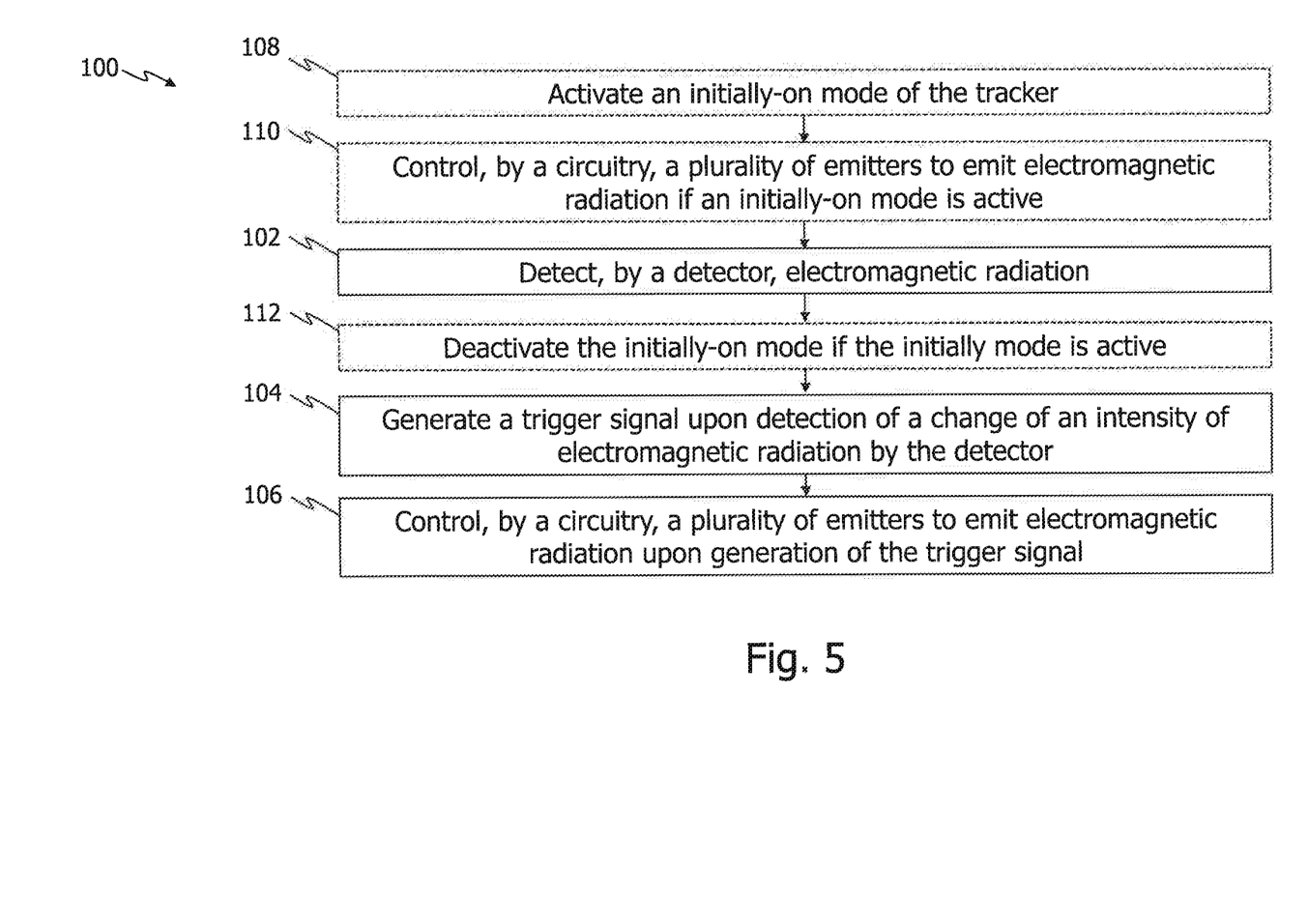
FIG. 5 shows a flow diagram of an embodiment of a method for operating a tracker.

FIG. 5 shows a flow diagram 100 of the method embodiment of operating the tracker 12.

The method comprises in step 102 detecting, by the detector 32, electromagnetic radiation. The electromagnetic radiation may be detected by a radiation-sensitive element of the phototransistor 32A or the photodiode 40 as described above.

The method further comprises in step 104 generating a trigger signal upon detection of a change of an intensity of electromagnetic radiation by the detector 32. The trigger signal may be the electrical signal generated by the radiation-sensitive element of the phototransistor 32A or the photodiode 40. Examples of circuits 36 for which the electrical signal is the trigger signal are described above with reference to FIGS. 3A, 3B, 4A, and 4B. Alternatively, the electrical signal may be modified in order to generate the trigger signal. The modification may comprise at least one of generating a trigger signal having a predetermined duration, generating an inverse signal, signal amplification, and noise filtering. Examples of circuits 36 that modify the electrical signal in order to generate the trigger signal are described above with reference to FIGS. 3C to 3F.

The trigger signal may be generated upon a change of the intensity of electromagnetic radiation in form of an increase of the intensity as well as a decrease of the intensity. Alternatively, the trigger signal may be generated only upon detection of an increase of the intensity of electromagnetic radiation by the detector. Further alternatively, the trigger signal may be generated only upon detection of a decrease of the intensity of electromagnetic radiation by the detector. An increase of the intensity of electromagnetic radiation may comprise at least one of the intensity exceeding an intensity threshold and a rate of change of the intensity exceeding a threshold. A decrease of the intensity of electromagnetic radiation may comprise at least one of the intensity falling below an intensity threshold and the rate of change falling below a threshold.

The method also comprises in step 106 controlling, by the circuitry 36, the plurality of emitters 34 to emit electromagnetic radiation responsive to the trigger signal. The circuitry 36 is configured to control the plurality of emitters 34 to emit electromagnetic radiation for a duration in which the trigger signal is generated. The circuitry 36 may be configured to generate the trigger signal for a duration that the detector 32 is subsequently not detecting a change of the intensity of electromagnetic radiation. For example, the detector 32 initially detects an increase of the intensity of electromagnetic radiation to a high value and therefore the circuitry 36 generates a trigger signal. As long as the detector 32 continues to detect the intensity of electromagnetic radiation at the high value, the circuitry 36 keeps generating the trigger signal. Once the detector 32 detects that the intensity of electromagnetic radiation falls below the high value (i.e., the intensity changes), the circuitry 36 stops generating the trigger signal.

Alternatively, the circuitry 36 may be configured to generate the trigger signal for a predetermined time duration. The time duration may therefore be different from the time duration of the pulse emitted by the source of electromagnetic radiation 16. The time duration may in particular be shorter than the pulse duration so as to have a shorter on-cycle of the emitters 34, which is particular advantageous in case of a battery-operated tracker 12.

Optionally, the circuitry 36 may have an initially-on mode, wherein the emitters 34 are emitting electromagnetic radiation, and the initially-on mode is deactivated upon a first detection of electromagnetic radiation by the detector 32. In such a case, the method may further comprise in step 110 activating the initially-on mode of the tracker 12. The initially-on mode may be activated by providing power to the tracker 12 (e.g., by inserting a battery or by attaching the tracker 12 to a surgical instrument that provides power, or by operating a switch of the tracker 12). The method then further comprises in step 110 controlling, by the circuitry 36, the plurality of emitters 34 to emit electromagnetic radiation in the initially-on mode. In such a case, the method 100 further comprises in step 112 deactivating the initially-on mode upon detecting electromagnetic radiation by the detector 32 if the initially mode is active. As a result, the emitters 34 initially emit electromagnetic radiation even when the circuitry 36 is not triggered by electromagnetic radiation. Once the detector 32 detects a first initial pulse of electromagnetic radiation, emission of the emitters 34 is instead subsequently triggered by (absence or presence of) consecutive pulses of electromagnetic radiation. A tracker 12 with such circuitry 36 when in initially-on mode can be placed in a field of view of the camera 14, wherein the camera 14 can capture the electromagnetic radiation emitted by the emitters 34. Based on the captured image data, the processor 20 may determine that the tracker 12 has been placed in the field of view and instruct the controller 18 to initiate emission of pulses by the source of electromagnetic radiation 16. The user may communicate (e.g., with a user interface such as a keyboard and mouse) to the processor 20 that a triggerable tracker 12 as described herein is about to be placed in the field of view. Alternatively, the processor 20 may have access to a database with an identifier associated with the triggerable tracker 12. The processor 20 may then be configured to determine based on a comparison of the identifier with the captured image data that the tracker 12 can be triggered. The identifier may be at least one of a geometrical arrangement of the emitters 34 and a wavelength or spectrum emitted by the emitters 34. Once the processor 20 has identified the triggerable tracker 12, the processor 20 can instruct the controller 18 to initiate emission of pulses by the source of electromagnetic radiation 16.

As explained above, the camera 14 defines the exposure timing and the source of electromagnetic radiation 16 emits pulses that temporally overlap with the exposure timing and trigger the emitters 34 to emit electromagnetic radiation with the same or with a predetermined duration. In order to better understand temporal relationships between these different devices of the surgical tracking system 10, a time progression of the intensity of emission of the source of electromagnetic radiation 16 and the emitters 34 will now be described with reference to FIGS. 6A-F.

FIGS. 6A-F show diagrams of time progressions of exposure timing 42, intensity of electromagnetic radiation 44 of the source of electromagnetic radiation 16, and intensity of electromagnetic radiation 46 of the emitters 34.

The exposure timing 42 is depicted as a stripe with alternating white blocks 48 and black blocks 50, wherein the white blocks 48 represent exposure time durations and the black blocks 50 represent non-exposure time durations. A combination of a white and black block 48, 50 forms a frame. The amount of frames captured in a given period of time (such as in a second) is denoted as the frame rate. For example, the camera 14 may have a frame rate of 500 Hz with a frame duration of 2 ms. The frame duration may cover an exposure time duration of 300 μs and a non-exposure time of 1.7 ms.

The intensity of electromagnetic radiation 44 of the source of electromagnetic radiation 16 alternates between a low intensity (or zero intensity) and a high intensity. A dashed line indicates a low or zero intensity for the intensity of electromagnetic radiation 44 of the source of electromagnetic radiation 16 and the intensity of electromagnetic radiation 46 of the emitters 34.

Figure 6A:
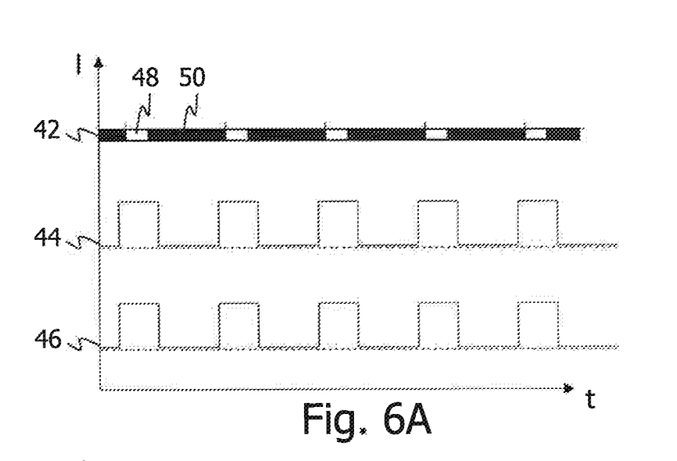
FIG. 6A shows a time progression diagram for which the circuitry of the tracker generates a trigger signal only for a duration that the detector is detecting electromagnetic radiation.

FIG. 6A shows a time progression diagram in which the circuitry 36 of the tracker 12 generates a trigger signal only for a duration that the detector 32 is detecting electromagnetic radiation. To be more specific, the circuitry 36 is configured to generate a trigger signal only upon detection of an increase of the intensity of electromagnetic radiation detected by the detector 32 and to generate the trigger signal for a duration that the detector 32 is subsequently not detecting a change of the intensity of electromagnetic radiation. Examples of such a circuitry 36 are described above with reference to FIGS. 3A, 3B, 4A, and 4B.

The pulses of the electromagnetic radiation 44 are emitted in synchronicity with the exposure timings such that the intensity alternates with the same periodicity as the framerate of the camera 14. As illustrated in FIG. 6A, the switching times of the circuitry 36 are negligible.

For the example depicted in FIG. 6A, the pulse duration is longer than the exposure time duration. Alternatively, the pulse duration may be shorter than the exposure time duration. A shorter pulse duration may, for example, be possible if a sensitivity of the image sensor 24 is sufficiently high and/or an intensity of electromagnetic radiation emitted by the emitters 34 is sufficiently high. The controller 18 may be configured to control (e.g., adjust) the pulse duration to an intensity of electromagnetic radiation emitted by the emitters 34. The controller 18 may be configured to adjust the pulse duration according to a function inversely proportional to the intensity of electromagnetic radiation emitted by the emitters. As a result, the power consumption of the tracker 12 can be reduced. Furthermore, the pulse duration in FIG. 6A covers each entire exposure time duration. Alternatively, the pulse duration covers only a portion of the exposure time duration due to a temporal offset and/or a shorter pulse duration relative to the exposure time duration. During the exposure time duration (and partially for the non-exposure time durations), the intensity of electromagnetic radiation 44 of the source of electromagnetic radiation 16 is larger compared to the low or zero intensity.

When the pulse of electromagnetic radiation 44 of the source of electromagnetic radiation 16 is detected by the detector 32 of the tracker 12, the circuitry 36 of the tracker 12 generates a trigger signal for a duration that the detector 32 is subsequently not detecting a change of the intensity of electromagnetic radiation, i.e. for the duration of the pulse of electromagnetic radiation 44 of the source of electromagnetic radiation 16. In the example depicted in FIG. 6A, the circuitry is configured to generate the trigger signal only for a duration that the detector 32 is detecting electromagnetic radiation. Since the trigger signal causes the circuitry 36 to control the emitters 34 to emit electromagnetic radiation, the emitters 34 emit electromagnetic radiation for the pulse duration of the source of electromagnetic radiation 16.

The pulses emitted by the source of electromagnetic radiation 16 temporally overlap with the exposure time durations of the camera 14. Therefore, the emitters 34 are triggered to emit electromagnetic at a time in which the at least one image sensor 24 is exposed to electromagnetic radiation. The emitters 34 do not emit electromagnetic radiation at least for a part of the non-exposure time duration. As a result, the tracker 12 is energy efficient with a simple setup of the circuitry 36.

Figure 6B:
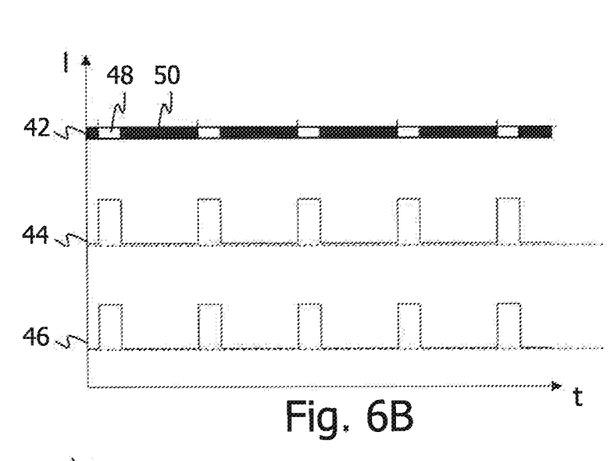
FIG. 6B shows a time progression diagram for which the circuitry of the tracker generates a trigger signal only for a duration that the detector is detecting electromagnetic radiation, wherein the pulse of the source of electromagnetic radiation has the same duration and starting time as an exposure time duration of a camera.

FIG. 6B shows a time progression diagram in which the circuitry 36 of the tracker 12 generates a trigger signal only for a duration that the detector 32 is detecting electromagnetic radiation. Similar as shown in FIG. 6A, the circuitry 36 is configured to generate the trigger signal only upon detection of an increase of the intensity of electromagnetic radiation by the detector 32 and for a duration that the detector 32 is subsequently not detecting a change of the intensity of electromagnetic radiation. The example depicted in FIG. 6B differs from the one depicted in FIG. 6A essentially in that the source of electromagnetic radiation 16 emits pulses of electromagnetic radiation with the same duration and starting time as the exposure time duration. In FIG. 6B, this is illustrated by the white block coinciding with the duration of the high intensity of electromagnetic radiation 44 of the source of electromagnetic radiation 16.

As a result, the emitters 34 only emit electromagnetic radiation while the at least one image sensor 24 is exposed to electromagnetic radiation and the emitters 34 do not emit electromagnetic radiation while the at least one image sensor 24 is not exposed to electromagnetic radiation. Therefore, exposure of the image sensor 24 is maximized for the least amount of power output of the tracker 12.

Figure 6C:
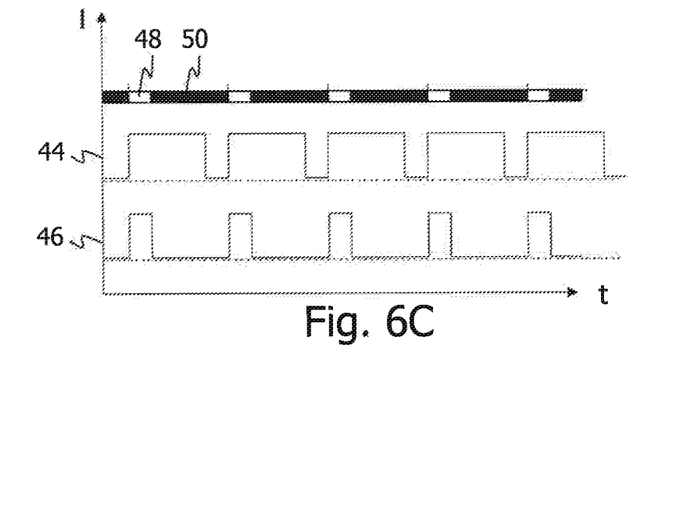
FIG. 6C shows a time progression diagram for which the circuitry of the tracker generates a trigger signal for a predetermined time duration.

FIG. 6C shows a time progression diagram in which the circuitry 36 of the tracker 12 generates a trigger signal for a predetermined time duration. An example for such a circuitry 36 is described above with reference to FIG. 3C. The duration of the pulses of the source of electromagnetic radiation 16 are longer than the exposure time duration. The predetermined time duration of emissions of the emitter 34 is set up for the tracker independently of the source of electromagnetic radiation 16. A predetermined duration may be used in combination with a source of electromagnetic radiation 16 that emits pulses with a duration what would translate to emission of the emitters 34 for a duration that is longer than the exposure time duration and therefore longer than necessary. The circuitry 36 is configured to generate the trigger signal for a predetermined duration that is shorter than the pulse of electromagnetic radiation while still being long enough to ensure sufficient exposure of the at least one image sensor 24. Such a circuitry 36 is therefore more energy efficient.

The source of electromagnetic radiation 16 is often used in combination with passive trackers that reflect the electromagnetic radiation back to the camera 14 so that they can be tracked by the tracking system 10. Consequently, the pulses of electromagnetic radiation have to be emitted so as to overlap with the exposure time durations of the camera 14, as illustrated in FIGS. 6A-6C (see reference numerals 42 and 44). In case an active tracker is used, such as the tracker 12, the overlap as illustrated in FIGS. 6A-6C is not required and the pulses of electromagnetic radiation can be emitted without any overlap with the exposure time durations of the camera 14, as illustrated in FIG. 6D.

Figure 6D:
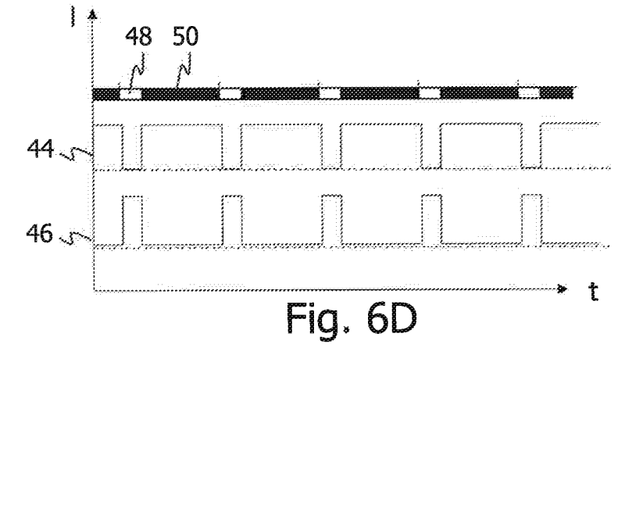
FIG. 6D shows a time progression diagram for which the circuitry of the tracker is configured to generate a trigger signal upon detection of absence of electromagnetic radiation by the detector.

FIG. 6D shows a time progression diagram in which the circuitry 36 of the tracker 12 is configured to generate a trigger signal upon detection of absence of electromagnetic radiation by the detector 32. An example for such a circuitry 36 is depicted in FIG. 3D. The controller 18 is configured to control the source of electromagnetic radiation 16 to emit pulses during non-exposure time durations and to not emit pulses during exposure time durations. Since the circuitry 36 is configured to generate the trigger signal upon detection of absence of electromagnetic radiation by the detector 32, the circuitry 36 controls the emitters 34 to emit electromagnetic radiation when the source of electromagnetic radiation 16 does not emit electromagnetic radiation 16. The electromagnetic radiation emitted by the source of electromagnetic radiation 16 may reflect of other surfaces at the surgical site, which may result in interfering noise captured by the at least one image sensor 24. Since the source of electromagnetic radiation 16 emits pulses during non-exposure time durations, the interfering noise is reduced. Therefore, this type of generation of a trigger signal may increase tracking accuracy.

In the embodiment depicted in FIG. 6D, the circuitry 36 is configured to generate a trigger signal upon detection of a decrease of the intensity of electromagnetic radiation to zero. Alternatively, the circuitry 36 may be configured to generate a trigger signal upon detection of a decrease of the intensity of electromagnetic radiation to a value larger than zero. The detection of a decrease of an intensity of electromagnetic radiation may be based on a threshold criterion. The threshold criterion may comprise a decrease below a lower intensity threshold for radiant intensity. Alternatively, the threshold criterion may comprise a threshold for a rate of change of radiant intensity.

Figure 6E:
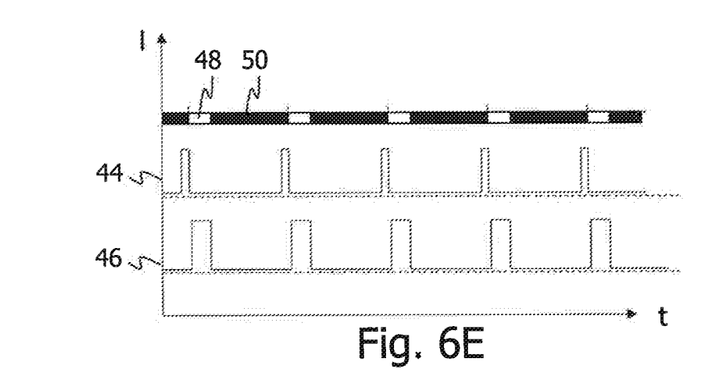
FIG. 6E shows a time progression diagram in which the circuitry of the tracker is configured to generate a trigger signal only upon detection of a decrease of electromagnetic radiation by the detector and to generate the trigger signal for a predetermined time duration.

FIG. 6E shows a time progression diagram in which the circuitry 36 of the tracker 12 is configured to generate a trigger signal only upon detection of a decrease of electromagnetic radiation by the detector 32 and to generate the trigger signal for a predetermined time duration. An example of such a circuitry 36 is described above with reference to FIG. 3E. Since the duration of the trigger signal is independent of the duration of a pulse of electromagnetic radiation, the pulse duration can be shortened significantly (e.g., to protect the eyes of the surgeon, in particular if the pulse of electromagnetic radiation comprises infrared light that is unperceivable for the human eye).

Figure 6F:
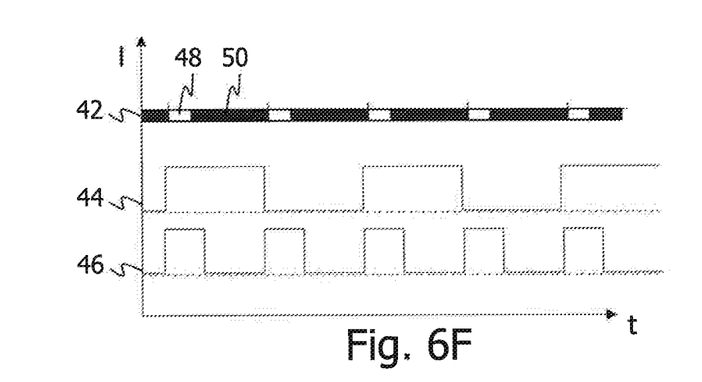
FIG. 6F shows a time progression diagram in which the circuitry of the tracker is configured to generate a trigger signal upon a change of the intensity of electromagnetic radiation by the detector, wherein the change of the intensity can occur in form of an increase as well as in form of a decrease.

FIG. 6F shows a time progression diagram in which the circuitry 36 of the tracker 12 is configured to generate a trigger signal upon a change of the intensity of electromagnetic radiation by the detector, wherein the intensity change can occur in form of an increase as well as in form of a decrease. As can be seen in FIG. 6F, in both cases the circuitry 36 generates a trigger signal for a predetermined duration.

Alternatively, the circuitry 36 may be configured to generate a first trigger signal upon detecting an increase of the intensity and a second trigger signal upon detecting a decrease of the intensity, wherein the circuitry is configured to generate a trigger signal for the duration from the first to the second trigger signal.

It is be noted that FIG. 6E shows an example in which the first frequency, which defines the exposure timing, is twice the second frequency, which defines the frequency in which the pulsed electromagnetic radiation is emitted. Therefore, emission of the pulses of electromagnetic radiation in synchronicity with the exposure timing does not require identity between the first and second frequency. The first frequency may instead be a multiple of the second frequency (or vice versa).

The tracker 12 depicted in FIGS. 2A and 2B has a single face and the detector 32 is assigned to all emitters 34 of the tracker 12. In same variants, the tracker 12 may have multiple subsets of emitters 34 to allow switching between different arrangements of emitters 34 and/or for a tracker 12 with multiple faces.

Figure 7A:
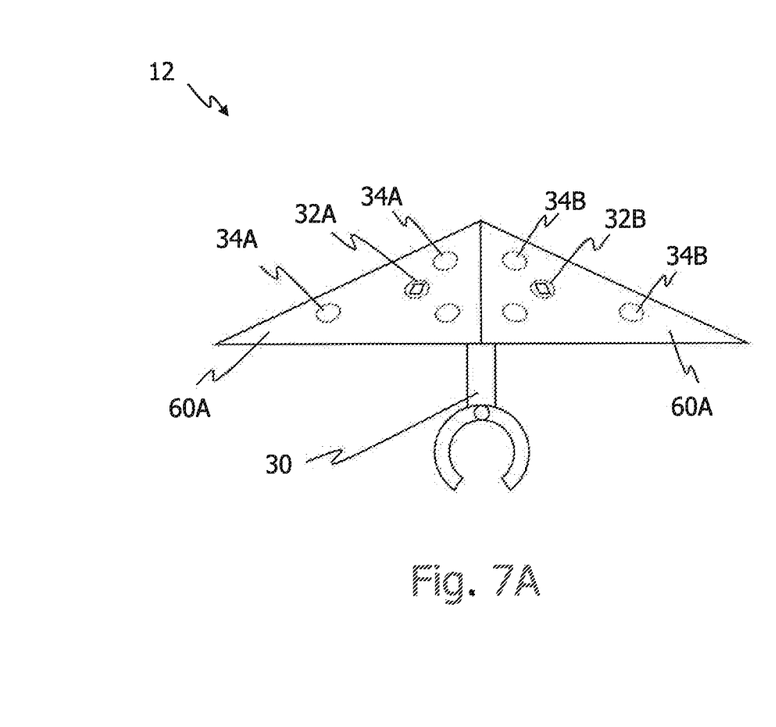
FIG. 7A shows a side view of second embodiment of the tracker.
Figure 7B:
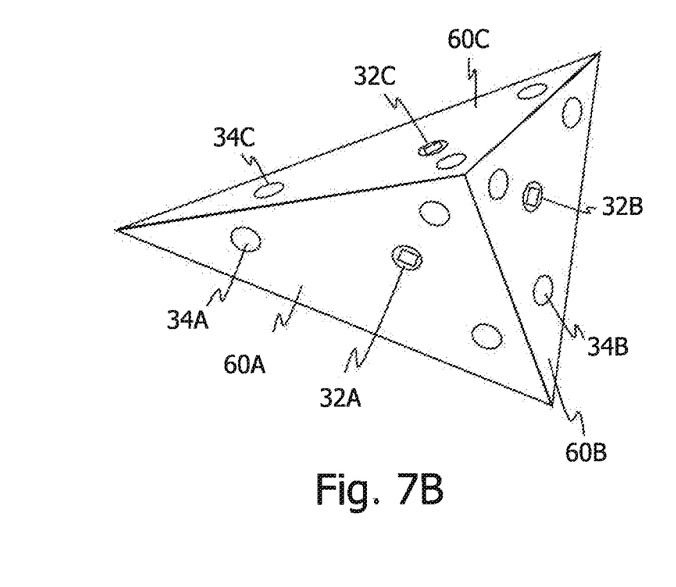
FIG. 7B shows a perspective view of the tracker depicted in FIG. 7A.

FIG. 7A shows a side view of a second embodiment of a tracker 12. FIG. 7B shows a perspective view of the tracker 12 depicted in FIG. 7A. The tracker 12 shown in FIGS. 7A, B has three faces 60A, 60B, and 60C. Alternatively, the tracker 12 may have a different number of faces, such as two, four, five, or more. The faces 60A, 60B, 60C are arranged at an angle to each other. The faces 60A, 60B, 60C may be arranged at an angle in a range of 170° to 10°, such as 120° to 90°.

The tracker 12 of FIGS. 7A and 7B comprises three subsets of emitters 34A, 34B, 34C, wherein each face 60A, 60B, 60C supports one of the subsets of emitters 34A, 34, 34C. In the example depicted in FIGS. 7A and 7B, each subset has three emitters such that the tracker 12 has a total of nine emitters 34A, 34B, 34C. Alternatively, at least one of the subsets may have two, four, five, or more emitters 34.

The tracker 12 further comprises three detectors 32A, 32B, 32C. Each of the faces 60A, 60B, 60C supports one subset of emitters 34A, 34B, 34C and one of the three detectors 32A, 32B, 32C, wherein the detector 32A, 32B, 32C of a dedicated face 60A, 60B, 60C is associated with the emitters 34A, 34B, 34C of the dedicated face 60A, 60B, 60C. For example, on a first face 60A are arranged a first detector 32A and a first subset comprising three emitters 34A, wherein the first detector 32A is associated with the emitters 34A of the first subset.

As a result, the emitters 34A of the first subset are only triggered by the first detector 32A, the emitters 34B of the second subset are only triggered by the second detector 32B, and the emitters 34C of the third subset are only triggered by the third detector 32C. Any trigger mechanism described herein (e.g., with reference to FIGS. 6A to 6F) can be applied to the detectors 32A, 32B, 32C and the associated emitters 34A, 34B, 34C. The trigger mechanism may be identical or different for each face 60A, 60B, 60C. A tracker 12 with multiple faces is visible from a larger range of angles and therefore improves tracking accuracy for larger ranges of motion of the tracker 12. Since a detector 32A, 32B, 32C facing away from the source of electromagnetic radiation 16 is not triggered (or at least has a lower probability of being triggered), no additional communication between the tracker 12 and the camera 14 regarding the orientation of the tracker 12 is required, and power consumption is reduced.

The tracker 12 as described herein is configured to emit pulsed electromagnetic radiation, which decreases power consumption and weight of the tracker 12 (as the power source can be dimensioned with less capacity). The pulses can be synchronized with the exposure timing of the camera, making sure that the pulses emitted by the tracker 12 can be captured by the camera 14. In this regard, the tracker 12 can be synchronized with the camera 14 without requiring an additional data communication device. The circuit 36 described herein is simply triggered by electromagnetic radiation (or absence thereof) and requires no data communication.

Furthermore, a single detector 32 can be used to trigger multiple or all emitters 34, resulting in a more lightweight tracker 12.

The tracker 12 can in particular be configured as a low-cost and disposable item. For example, the tracker 12 may comprise an activating switch that can be activated only once, to safely prevent further uses.

The features described in relation to the exemplary embodiments shown in the drawings can be readily combined to result in different embodiments. It is apparent, therefore, that the present disclosure may be varied in many ways. Such variations are not to be regarded as a departure from the scope of the invention as defined by the claims appended hereto.

The invention claimed is:

1. A tracker for a surgical tracking system, the tracker comprising:
   an interface configured to attach the tracker to a surgical object that is to be tracked; and
   circuitry comprising:
      a detector configured to detect electromagnetic radiation, wherein the circuitry is configured to generate a trigger signal upon detection of a change of an intensity of electromagnetic radiation by the detector; and
      a plurality of emitters configured to emit electromagnetic radiation,
   wherein the circuitry is configured to control each of the plurality of emitters to simultaneously emit the electromagnetic radiation including the one of infrared light, visible light, ultraviolet light, and X-rays responsive to the trigger signal.

2. The tracker according to claim 1, wherein the circuitry is configured to generate the trigger signal only upon detection of an increase of the intensity of electromagnetic radiation by the detector.

3. The tracker according to claim 1, wherein the circuitry is configured to generate the trigger signal only upon detection of a decrease of the intensity of electromagnetic radiation by the detector.

4. The tracker according to claim 1, wherein the circuitry is configured to generate the trigger signal for a duration that the detector is subsequently not detecting a change of the intensity of electromagnetic radiation.

5. The tracker according to claim 1, wherein the circuitry is configured to generate the trigger signal for a predetermined time duration.

6. The tracker according to claim 1, wherein the detector comprises a single radiation-sensitive element associated with at least a subset of emitters, wherein the subset comprises more than one emitter of the plurality of emitters.

7. The tracker according to claim 1, wherein the tracker comprises at least one battery for powering the circuitry.

8. The tracker according to claim 1, further comprising a wireless power reception device configured to receive power wirelessly.

9. The tracker according to claim 1, wherein the circuitry comprises a switch configured to control a current passing through the emitters responsive to the trigger signal.

10. The tracker according to claim 1, wherein at least one of (i) the detector is configured to detected infrared light, and (ii) the plurality of emitters are configured to emit infrared light.

11. The tracker according to claim 1, wherein each of the plurality of emitters comprises a light emitting diode, LED, and wherein the circuitry is configured to limit a current through each of the LEDs to a current below 10 milliamperes.

12. A surgical tracking system comprising:
   a tracker comprising:
      an interface configured to attach the tracker to a surgical object that is to be tracked; and
      circuitry comprising:
         a detector configured to detect electromagnetic radiation, wherein the circuitry is configured to generate a trigger signal upon detection of a change of an intensity of electromagnetic radiation by the detector; and
         a plurality of emitters configured to emit electromagnetic radiation,
      wherein the circuitry is configured to control each of the plurality of emitters to simultaneously emit the electromagnetic radiation including the one of infrared light, visible light, ultraviolet light, and X-rays responsive to the trigger signal;
   a camera with at least one image sensor configured to detect the electromagnetic radiation emitted by the tracker of the surgical tracking system, and to generate image data based on the detected electromagnetic radiation, the camera having an exposure timing defining exposure time durations in which the at least one image sensor of the camera is sensitive to the electromagnetic radiation emitted by the tracker;
   a source of electromagnetic radiation;
   a controller configured to control the source of electromagnetic radiation to emit pulses of electromagnetic radiation in synchronicity with the exposure timing; and
   a processor configured to determine positional data of the tracker based on the image data.

13. The surgical tracking system according to claim 12, wherein the controller is configured to control a pulse duration of the pulsed electromagnetic radiation to lie between half and twice the exposure time of the camera.

14. The surgical tracking system according to claim 12, wherein the controller is configured to control the source of electromagnetic radiation to emit pulses of electromagnetic radiation at least during some of the exposure time durations.

15. The surgical tracking system according to claim 12, wherein the controller is configured to control the source of electromagnetic radiation to emit pulses of electromagnetic radiation at least between some of the exposure time durations.

16. The surgical tracking system according to claim 12, wherein the exposure time duration is less than 1 millisecond.

17. The surgical tracking system according to claim 12, wherein the source of electromagnetic radiation is configured to flood an entire surgical site in which the tracker is operated with electromagnetic radiation.

18. The surgical tracking system according to claim 12, further comprising an output device configured to output navigation instructions based on the positional data of the tracker as determined by the processor.

19. A method for operating a tracker attached to a surgical object, wherein the tracker comprises circuitry comprising a detector and a plurality of emitters configured to emit electromagnetic radiation, the method comprising:

generating, by the circuitry, a trigger signal upon detection of a change of an intensity of electromagnetic radiation by the detector; and controlling, by the circuitry, each of the plurality of emitters to simultaneously emit electromagnetic radiation including one of infrared light, visible light, ultraviolet light, and X-rays responsive to the trigger signal.

20. The method of claim 19, further comprising:

detecting the electromagnetic radiation emitted by the tracker; and generating image data based on the detected electromagnetic radiation, using a camera having an exposure timing defining exposure time durations in which at least one image sensor of the camera is sensitive to the electromagnetic radiation.

* * * * *